(12) United States Patent
Adem et al.

(10) Patent No.: US 11,713,290 B2
(45) Date of Patent: Aug. 1, 2023

(54) CYCLOHEPTYLAMINE DERIVATIVES AS ANTI-DIABETIC AGENTS

(71) Applicant: UNITED ARAB EMIRATES UNIVERSITY, Al Ain (AE)

(72) Inventors: Abdu Adem, Al Ain (AE); Shaikha S. Al Neyadi, Al Ain (AE); Ibrahim M. Abdou, Al Ain (AE); Alaa A. Salem, Al Ain (AE); Naheed Amir, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 169 days.

(21) Appl. No.: 17/386,279

(22) Filed: Jul. 27, 2021

(65) Prior Publication Data
US 2021/0355074 A1 Nov. 18, 2021

Related U.S. Application Data

(62) Division of application No. 16/866,856, filed on May 5, 2020, now Pat. No. 11,091,426.

(51) Int. Cl.
| | |
|---|---|
| *C07C 211/35* | (2006.01) |
| *C07C 279/26* | (2006.01) |
| *C07C 317/42* | (2006.01) |
| *C07C 279/16* | (2006.01) |
| *C07D 401/04* | (2006.01) |
| *C07D 239/48* | (2006.01) |

(52) U.S. Cl.
CPC .......... *C07C 211/35* (2013.01); *C07C 279/16* (2013.01); *C07C 279/26* (2013.01); *C07C 317/42* (2013.01); *C07D 239/48* (2013.01); *C07D 401/04* (2013.01)

(58) Field of Classification Search
CPC .. C07D 401/04; C07D 239/48; C07C 317/42; C07C 211/35; C07C 279/26; C07C 279/16
See application file for complete search history.

(56) References Cited

U.S. PATENT DOCUMENTS

| | | | |
|---|---|---|---|
| 3,355,355 A | 11/1967 | Stedman | |
| 7,411,093 B2 | 8/2008 | Boehringer et al. | |
| 9,133,110 B2 | 9/2015 | Kim et al. | |
| 9,284,296 B2 | 3/2016 | Palomo et al. | |
| 9,849,097 B2 * | 12/2017 | Nhamias | .................. A61P 5/50 |
| 2006/0258870 A1 | 11/2006 | Sen et al. | |

OTHER PUBLICATIONS

DeFronzo, R.A., Diabetologia, 1992. 35: p. 389-397.
M.M. Engelgau, L.S.G., J.B. Saaddine, J.P. Boyle, S.M. Benjamin, E. W. Gregg, E.F. Tierney, N. Rios-Burrows, A.H. Mokdad, E.S. Ford, G. Imperatore, K.M. Venkat Narayan, Ann. Intern. Med., 2004. 140: p. 945-950.
S. Wild, G.R., A. Green, R. Sicree, H. King and 1053., Diabetes Care, 2004. 27: p. 1047-1053.
P.F. Kador, J.H.K., N.E. Sharpless, J. Med. Chem., 1985. 28: p. 841-849.
G.B. Reddy, A.S., N. Balakrishna, R. Ayyagari, M. Padma, K. Viswanath, J.M. Petrash, Mol. Vis., 2008. 14: p. 593-601.
Mariappan G, S.B.P., Datta S, Kumar D and Haidar PK., Design, synthesis and antidiabetic evaluation of oxazolone derivatives. ChemInform, 2011. 123: p. 335- 341.
M. Dunlop, Kidney Int., 2000. 58: p. S3-S12.
M. Pyorala, H.M., P. Halonen, M. Laakso, K. Pyorala, Arterioscler., Thromb. Vasc. Biol., 2000. 20: p. 538-544.
Any identified foreign patents and/or publications have been properly submitted in parent application U.S. Appl. No. 16/866,856, filed May 5, 2020, the priority of which is claimed in its entirety.

* cited by examiner

*Primary Examiner* — Erich A Leeser
(74) *Attorney, Agent, or Firm* — Nath, Goldberg & Meyer; Richard C. Litman

(57) ABSTRACT

Cycloalkylamine derivatives may be used for preventing or treating diseases in humans, animals, and have demonstrated efficacy specifically in treating type 2 diabetes. In an embodiment, the cycloalkylamine derivatives can include a compound selected from the group consisting of cycloheptanamine salts, cyclohexanamine salts, cyclopentanamine salts 1-cycloheptyl-[4,4'-bipyridin]-1-ium, N1,N2-dicycloheptyloxalamide, 1-[3',5'-bis(trifluoromethyl)phenyl]-3-cycloheptylurea, 1,1'-(4-methyl-1,3-phenylene)bis(3-cycloheptylurea), 1-(2'-aminopyrimidin-4'-yl)-3-cycloheptylurea, 4-amino-N-(cycloheptylcarbamoyl)benzenesulfonamide, 4-(3'-cycloheptylureido)-N-(5"-methylisoxazol-3"-yl)benzenesulfonamide, N-(cycloheptylcarbamoyl)-4-methylbenzenesulfonamide, 1-cycloheptylguanidine hydrochloride, (E)-amino[(amino(cycloheptylamino)methylene)amino] methaniminium chloride, or a pharmaceutically acceptable salt thereof.

4 Claims, 11 Drawing Sheets

Cycloheptanaminium
chloride
(2a)

Cycloheptanaminium
bromide
(2b)

Cyclopentanaminium
chloride
(2c)

Cyclohexanaminium
chloride
(2d)

| Compound | R | R₁ |
|---|---|---|
| 9a | 3,5-bis(trifluoromethyl)phenyl | cycloheptyl |
| 9b | 2-methyl-1,4-phenyl | cycloheptyl |
| 9c | cycloheptyl | 2-amino-pyrimidin-4-yl |
| 9d | cycloheptyl | 4-aminophenylsulfonyl |
| 9e | cycloheptyl | 4-(N-(5-methylisoxazol-3-yl)sulfamoyl)phenyl |
| 9f | 4-methylphenylsulfonyl | cycloheptyl |

*FIG. 8*

CYCLOHEPTYLAMINE DERIVATIVES AS ANTI-DIABETIC AGENTS

CROSS REFERENCE TO RELATED APPLICATIONS

This application is a division of application Ser. No. 16/866,856, filed May 5, 2020, pending.

BACKGROUND

1. Field

The disclosure of the present patent application relates to cycloalkylamine derivatives that are demonstrated to treat certain diseases in humans or animals. In particular, cycloheptylamine derivatives, and compositions including the compounds, are shown to be effective in treating diabetes type-2.

2. Description of the Related Art

Increasing incidence of diabetes is considered to be one of the most common concerns in the medical field today. In the U.S. alone, in 2015, over 30 million Americans aged 18 years or older were estimated to have diagnosed or undiagnosed diabetes—about 9.4% of the adult population. Of these, about 23 million were estimated to have been diagnosed with diabetes, while over 7 million were undiagnosed. See "Statistics About Diabetes," American Diabetes Association, at https://www.diabetes.org/resources/statistics/statistics-about-diabetes. About 1.25 million American children and adults have type 1 diabetes; the rest have type 2 diabetes.

Diabetes is recognized as a chronic disease with high morbidity and mortality, posing an economic burden for developing countries [M. M. Engelgau, L. S. G., et al., Ann. Intern. Med., 140:945-950 (2004)]. A recent study by WHO reveals that there were approximately 200 million people globally, ranging age 20-80 years, suffering from diabetes. This figure is expected to increase to 366 million by the year 2030. Diabetic patients on prolonged exposure to uncontrolled hyperglycemia experience several diabetic complications such as retinopathy, neuropathy, cataracts, nephropathy and cardiovascular complication.

Several drugs, such as sulfonylureas (glipizide and glyburide) and biguanides (metformin) or a combination of metformin and sitagliptin, are presently available to reduce hyperglycemia in patients with diabetes mellitus. However, these drugs typically can cause significant side effects.

Thus, anti-diabetic agents solving the aforementioned problems is desired.

SUMMARY

Cycloalkylamine derivatives, as described herein, can provide effective anti-diabetic effects. These derivatives can include one or more compounds selected from the group consisting of cycloheptanamine hydrochloride, cycloheptanamine hydrobromide, 1-cycloheptyl-[4,4'-bipyridin]-1-ium chloride, and N1,N2-dicycloheptyloxalamide or a pharmaceutically acceptable salt thereof.

Several cycloalkylamine derivatives were demonstrated to provide effective hypoglycemic activity after administration of 1.0 µM/kg in Streptozotocin- (STZ-) induced diabetic rats. Blood glucose levels were measured and compared with a standard control drug.

The anti-diabetic activities of these novel derivatives showed better results than most commercially available anti-diabetic type-2 drugs. The in-vitro and in-vivo testing results showed that these novel compounds provide better efficacy in patients with type 2 diabetes. The methods used to synthesize these derivatives afforded better yields, in shorter time, yielding high purities.

These and other features of the present findings will become readily apparent upon further review of the following specification.

These and other features of the present invention will become readily apparent upon further review of the following specification and drawings.

BRIEF DESCRIPTION OF THE DRAWINGS

FIG. 8 is a table depicting the various R and $R_1$ substituents in cycloheptyl urea derivatives 9a-f.

Similar reference characters denote corresponding features consistently throughout the attached drawings.

DETAILED DESCRIPTION OF THE PREFERRED EMBODIMENTS

Cycloalkylamine derivatives described herein may be used for preventing or treating diseases in humans, animals and have demonstrated efficacy specifically in treating type 2 diabetes. According to one embodiment, the derivatives can provide effective hypoglycemic activity.

In an embodiment, the cycloalkylamine derivatives can include a compound selected from the group consisting of cyclohexanamine hydrochloride, cyclopentanamine hydrochloride, cycloheptanamine hydrochloride, cycloheptanamine hydrobromide, 1-cycloheptyl-[4,4'-bipyridin]-1-ium chloride, N1,N2-dicycloheptyloxalamide, 1-[3,5-bis(trifluoromethyl)phenyl]-3-cycloheptylurea, 1,1'-(4-methyl-1,3-phenylene)bis(3-cycloheptylurea), 1-(2-aminopyrimidin-4-yl)-3-cycloheptylurea, 4-amino-N-(cycloheptylcarbamoyl)benzenesulfonamide, 4-(3-cycloheptylureido)-N-(5-methylisoxazol-3-yl)benzenesulfonamide, N-(cycloheptylcarbamoyl)-4-methylbenzenesulfonamide, 1-cycloheptylguanidine hydrochloride, (E)-amino[(amino (cycloheptylamino)methylene)amino]methaniminium chloride, or a pharmaceutically acceptable salt thereof.

In an embodiment, the cycloalkylamine derivatives can include a compound having the following structural formula:

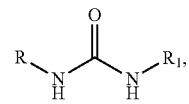

wherein
R is selected from the group consisting of

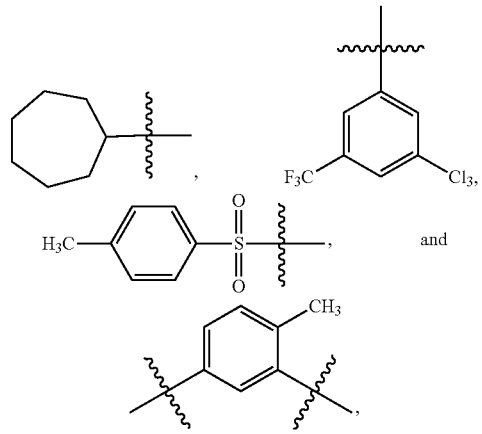

$R_1$ is selected from the group consisting of

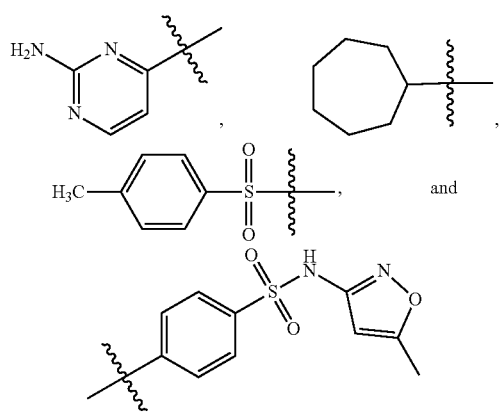

or a pharmaceutically acceptable salt thereof.

The cycloheptylamine derivatives synthesized in high yields, with high purity. The cycloheptylamine derivatives can be used in providing anti-diabetic effects. These derivatives may be prepared in any suitable pharmaceutical formulation, with any suitable pharmaceutical excipients, for administration to a patient in any suitable manner as generally known in the industry and that may be determined or designated by a medical practitioner treating the patient.

According to one embodiment, the cycloheptylamine derivatives provide effective treatment of fasting blood glucose.

Certain embodiments provide a method for the preparation and/or use of compounds 2a-d, as set forth in Example 4.

Figure 5:
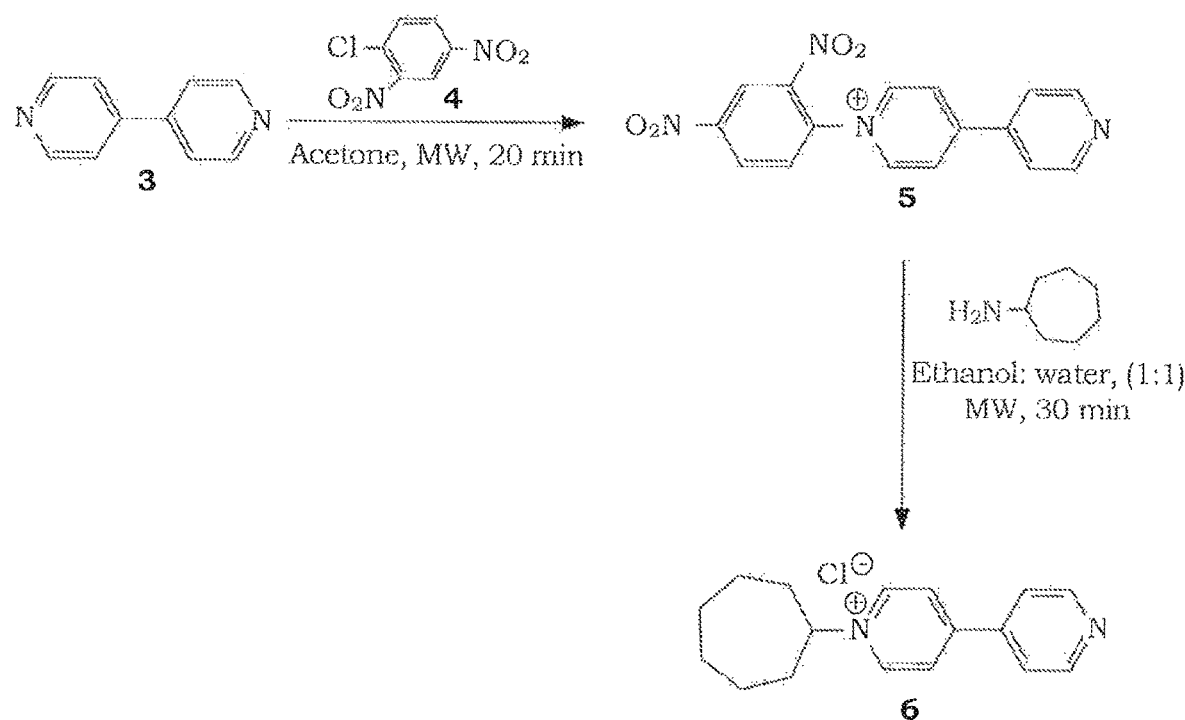
FIG. 5 depicts the synthesis scheme for compound 6.

Certain embodiments provide a method for the preparation and/or use of compound 6, as shown in FIG. 5 and described in Example 5.

Figure 6:
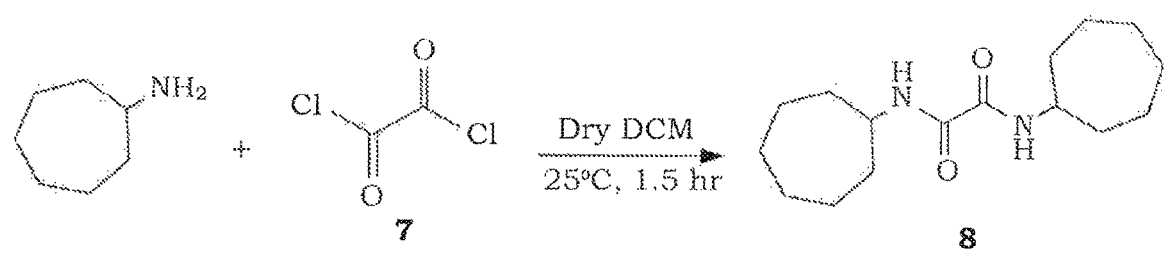
FIG. 6 depicts the synthesis scheme for compound 8.

Certain embodiments provide a method for the preparation and/or use of compound 8, as shown in FIG. 6 and as set forth in Example 7.

Figure 7:
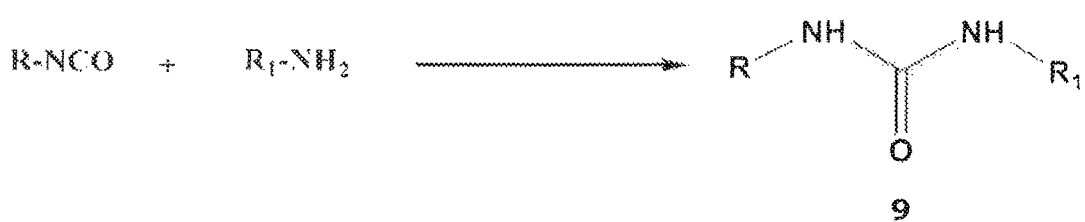
FIG. 7 depicts the general synthesis scheme for cycloheptyl urea derivatives 9a-f.

According to certain embodiments, the cycloheptylamine derivatives include cycloheptyl urea derivatives 9a-f, as shown in FIGS. 7 and 8, and as set forth in Example 8.

According to an embodiment, the cycloheptylamine derivatives include cycloheptyl guanidine derivative compound 10 and 11, as prepared in Example 9.

According to an embodiment, the cycloheptylamine derivatives include compounds 2a-d, as prepared in Example 4.

As described herein, in-vitro and in-vivo testing revealed that compound 2a demonstrated particular potency in providing anti-diabetic activity. Compound 2a produced significant reduction in blood glucose levels within 1 hour, and lasting as long as at least 8 hours. Compound 2a also significantly stimulated insulin secretions, both in the absence and presence of glucose.

The present findings are illustrated by the following Examples.

EXAMPLES

Pharmacology

The in-vitro and in-vivo testing results showed that cycloheptylamine derivatives provide better efficacy in rats with type 2 diabetes than many marketed anti-diabetic type-2 drugs. Several cycloheptylamine derivatives were demonstrated to provide effective hypoglycemic activity after administration of 1.0 μM/kg in Streptozotocin- (STZ-) induced diabetic rats. Blood glucose levels were measured and compared with a standard control drug. The test results showed that compound 2a produces both reductions in blood glucose levels and stimulation of insulin production.

Example 1

Evaluation of Some Novel Cycloalkylamine Hydrochoride Salts 2a-d on Fasting Blood Glucose (FBG)

The following cycloalkylamine hydrochloride salts 2a-d were synthesized and evaluated:

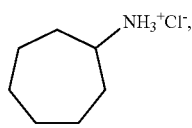

2a

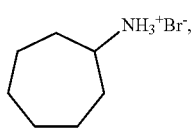

2b

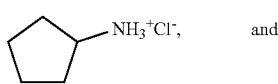

2c and

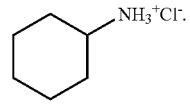

2d

Rats injected with (Streptozotocin STZ) showed significant increases in plasma glucose level and kidney weight along with decreases in serum insulin and body weight in comparison with non-diabetic rats. These symptoms indicated the development of diabetes characterized by chronic and persistently elevated plasma glucose levels.

STZ induces diabetes by selectively destroying the insulin producing pancreatic endocrine cells. Decreased body weight in STZ-induced diabetic rats is believed to be caused by dehydration, breakdown and catabolism of fats and proteins. Increased catabolic reactions upon administration of STZ results in muscle wasting and subsequently body weight loss.

Compound 2a was orally administrated to the treated groups of diabetic rats at a dose of 1.0 μM/kg. Glucose levels in their blood were followed over 8.0 hours. Diabetic rats treated with compound 2a showed significant reduction in blood glucose levels after one hour and up to 8 hours after treatment compared to control diabetic rats (FIGS. 1A-1D). Compounds 2b-d were orally administrated to the treated groups of diabetic rats at a dose of 1.0 μM/kg. Blood glucose levels were monitored at 0, 30 minutes, 60 minutes, 2 hours, 4 hours, 6 hours, 8 hours, and then again at 24 hours. See FIGS. 1A to 1D.

Example 2

The Effect of Compounds 2a on Insulin Secretion by βTC6 Cells

The secretion of insulin by βTC6 cells was measured using the high range insulin Sandwich ELISA kit. The 2.8 mM glucose gave a mild insulin response around 3000 pmol/l and was used in testing the effect of compounds 2a-d.

Figure 1A:
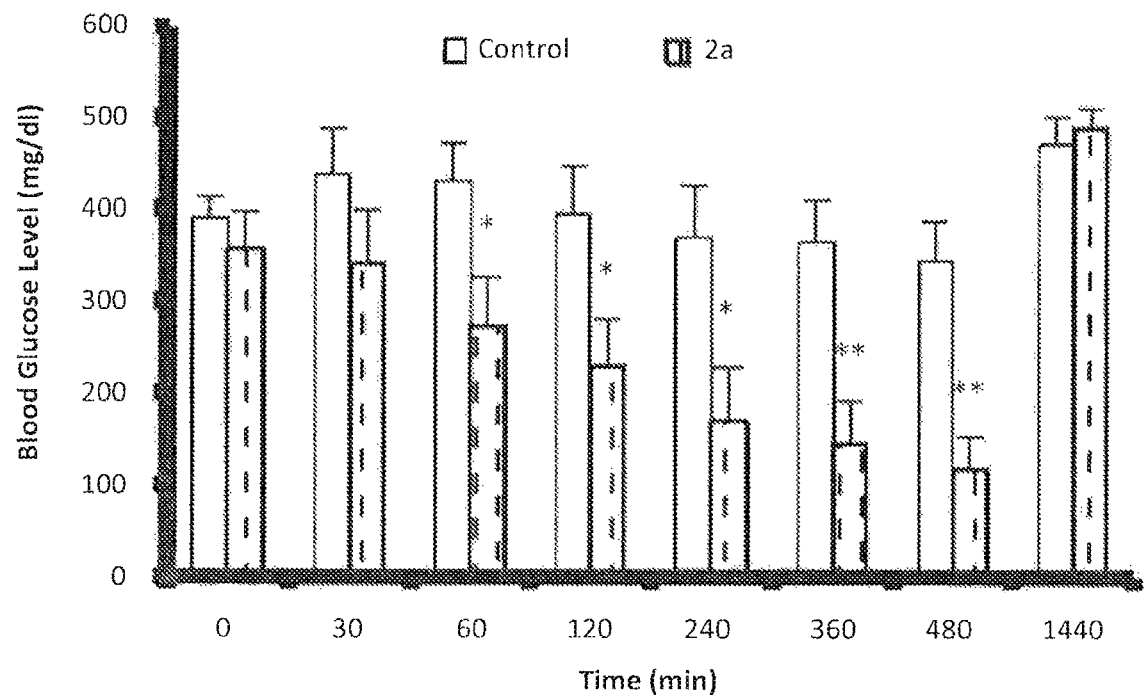
FIG. 1A is a bar graph showing in vivo anti-hyperglycemic effect on fasting blood glucose levels over time, ranging from 0 minute to 480 minutes, and at 1440 minutes, in STZ-induced diabetic rats, comparing a dose of 1.0 µM/kg compound 2a with control. Results are means±SEM; n=6 rats; *$P<0.05$, **$P<0.01$, vs. STZ control.
Figure 1B:
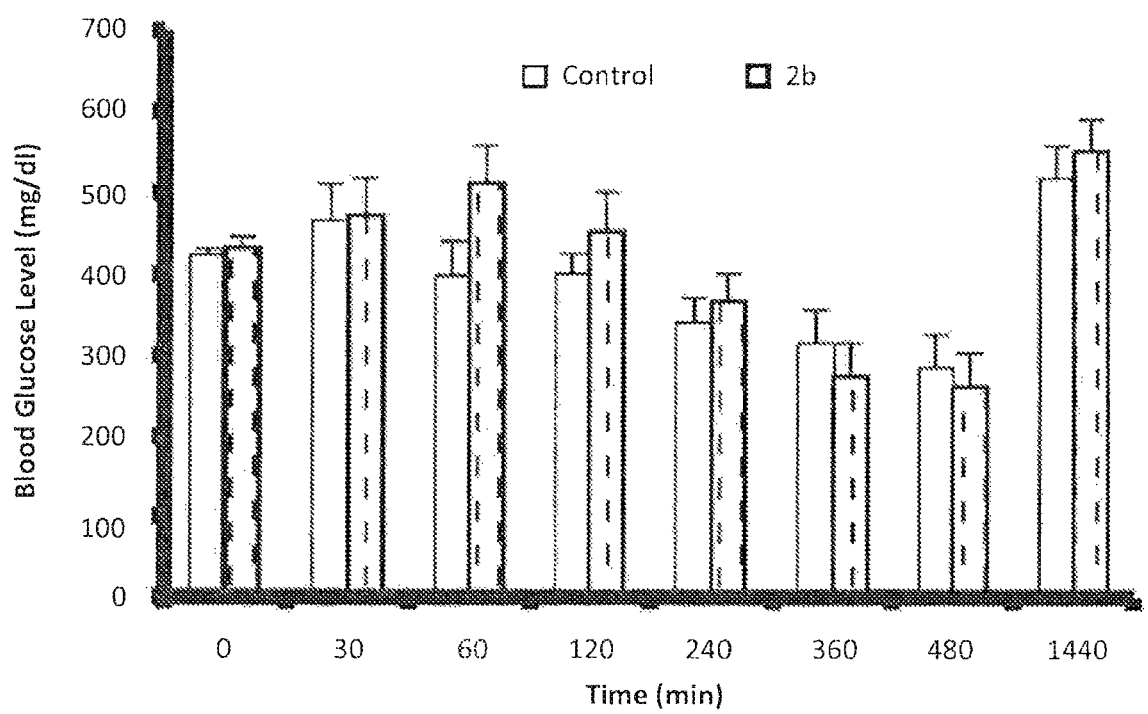
FIG. 1B is a bar graph showing in vivo anti-hyperglycemic effect on fasting blood glucose levels over time, ranging from 0 minute to 480 minutes, and at 1440 minutes, in STZ-induced diabetic rats, comparing a dose of 1.0 µM/kg compound 2b with control. Results are means±SEM; n=6 rats; *$P<0.05$, **$P<0.01$, vs. STZ control.
Figure 1C:
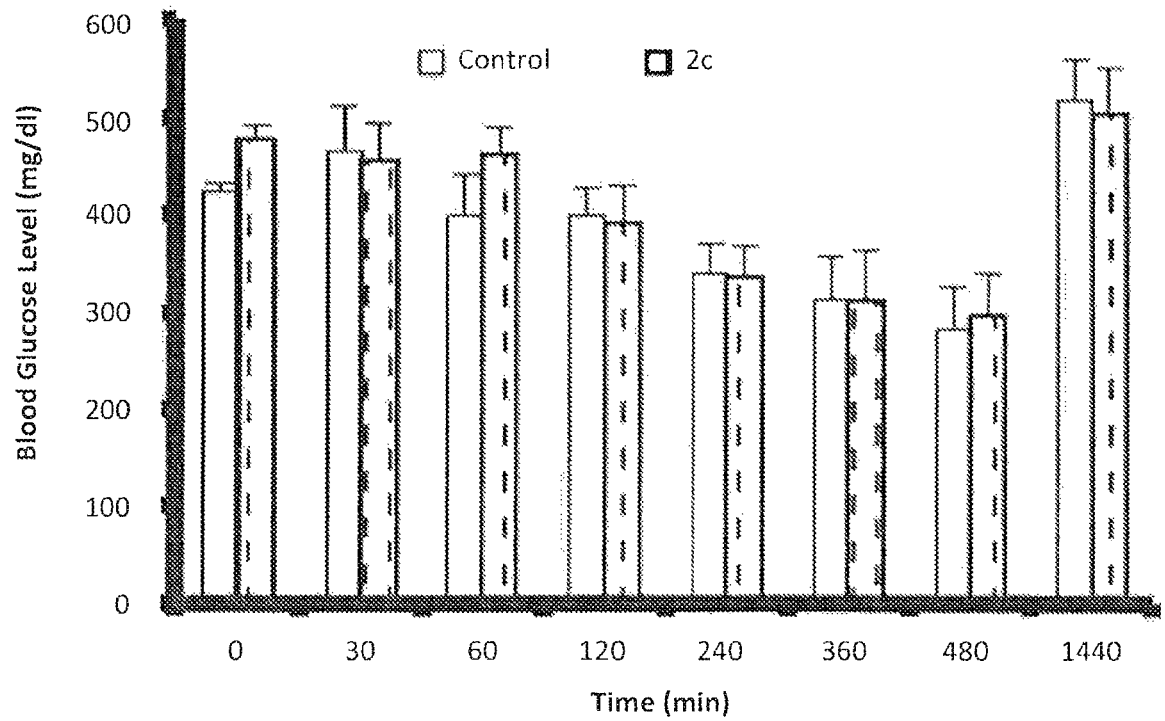
FIG. 1C is a bar graph showing in vivo anti-hyperglycemic effect on fasting blood glucose levels over time, ranging from 0 minute to 480 minutes, and at 1440 minutes, in STZ-induced diabetic rats, comparing an oral dose of 1.0 µM/kg compound 2c with control. Results are means±SEM; n=6 rats; *$P<0.05$, **$P<0.01$, vs. STZ control.
Figure 1D:
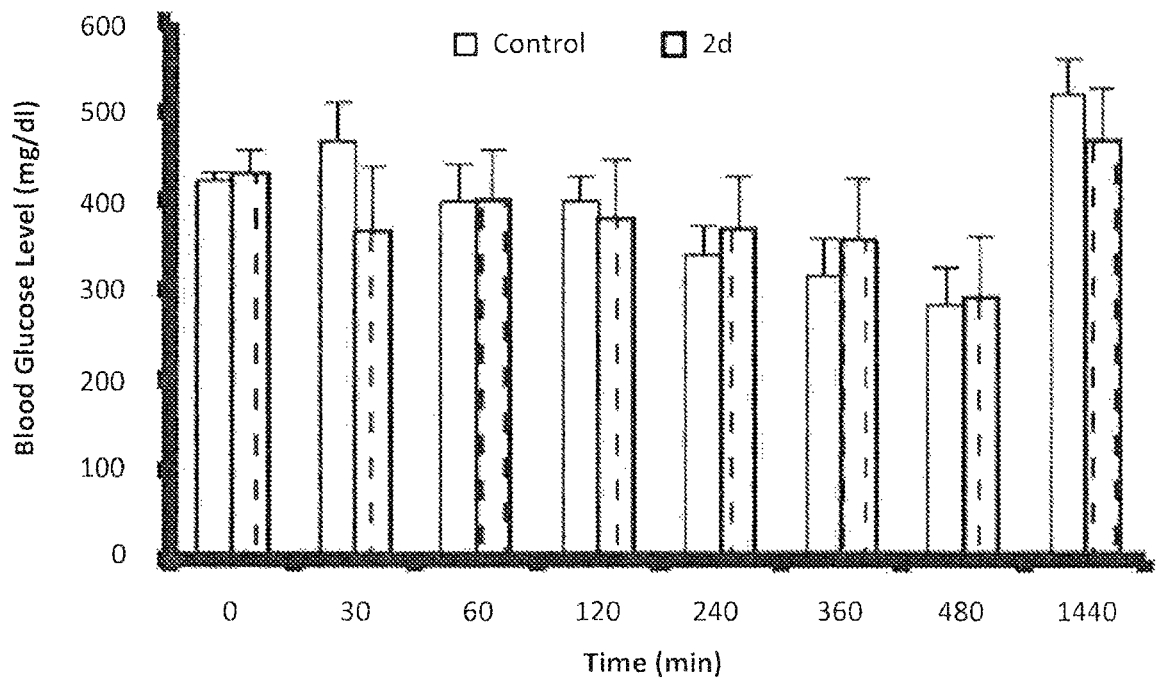
FIG. 1D is a bar graph showing in vivo anti-hyperglycemic effect on fasting blood glucose levels over time, ranging from 0 minutes to 480 minutes, and at 1440 minutes, in STZ-induced diabetic rats, comparing a dose of 1.0 µM/kg compound 2d with control. Results are means±SEM; n=6 rats; *$P<0.05$, **$P<0.01$, vs. STZ control.
Figure 2A:
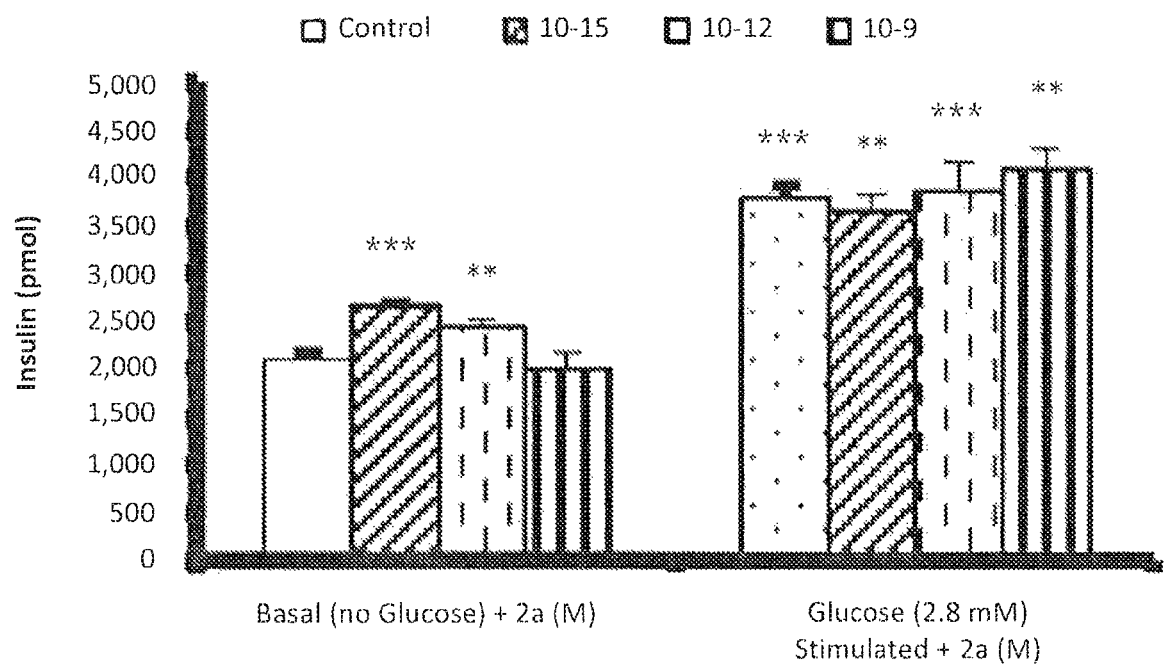
FIG. 2A is a bar graph showing the in vitro effects on insulin secretion of compound 2a at concentrations of $10^{-15}$, $10^{-12}$, and $10^{-9}$ M, compared to control, in both the absence and presence of 2.8 mM glucose. Results are means of triplicates±SEM; *$P<0.05$, $P<0.01$, *$P<0.001$, from relative basal control.

FIG. 2A show the in-vitro effects of the most potent compound 2a at $10^{-15}$, $10^{-12}$, and $10^{-9}$ M concentrations on insulin secretion in absence and presence of 2.8 mM glucose.

In the absence of glucose, concentrations of $10^{-15}$ and $10^{-12}$ M of compound 2a significantly stimulated insulin secretions compared to the basal control. In the presence of 2.8 mM glucose, concentrations ($10^{-15}$, $10^{-12}$, and $10^{-9}$ M) of compound 2a stimulated insulin secretions significantly compared to basal insulin secretion. Taken together the in-vivo and in-vitro results indicate that compound 2a is a potent anti-diabetic compound.

Figure 2B:
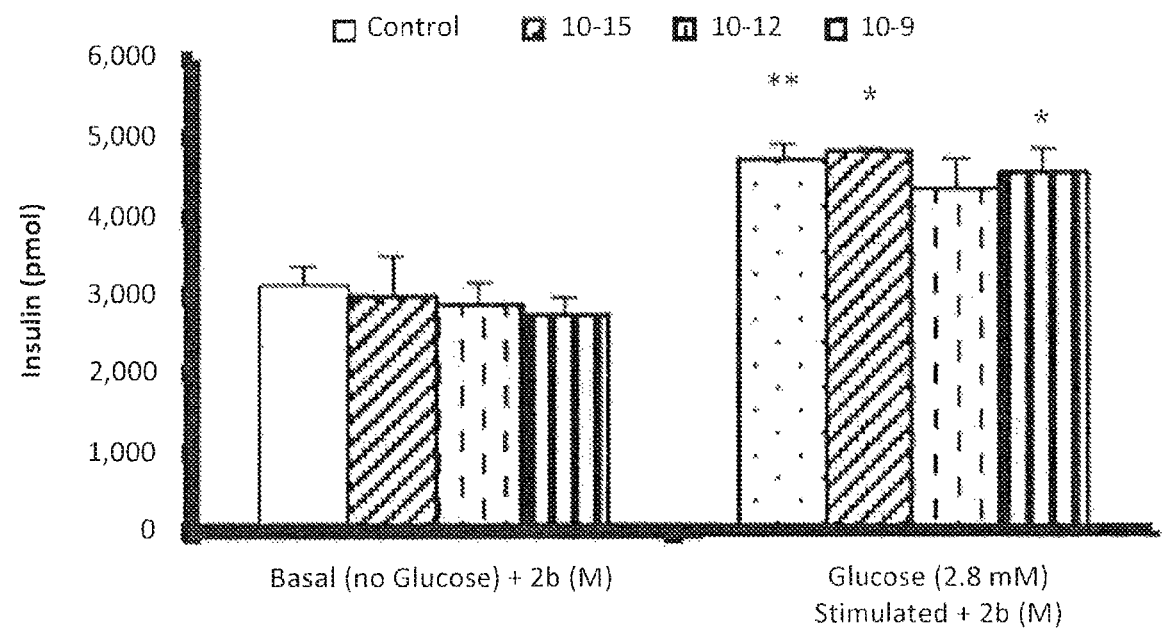
FIG. 2B is a bar graph showing the in vitro effects on insulin secretion of compound 2b at concentrations of $10^{-15}$, $10^{-12}$, and $10^{-9}$ M, compared to control, in both the absence and presence of 2.8 mM glucose. Results are means of triplicates±SEM; *$P<0.05$, $P<0.01$, *$P<0.001$, from relative basal control.
Figure 2C:
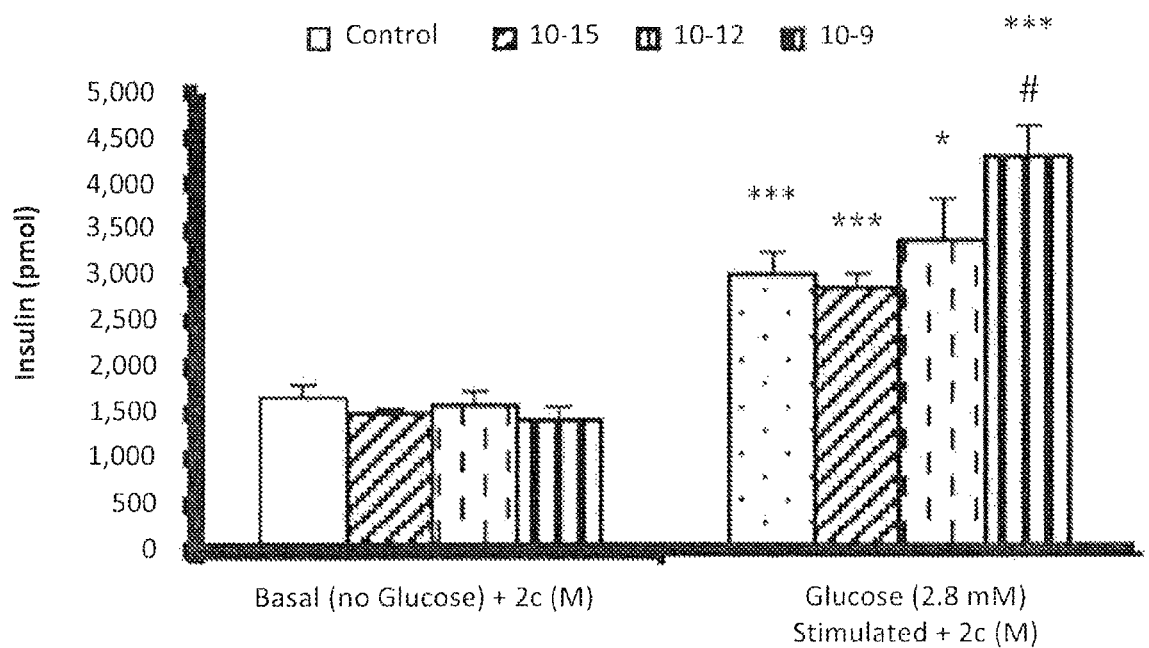
FIG. 2C is a bar graph showing the in vitro effects on insulin secretion of compound 2c at concentrations of $10^{-15}$, $10^{-12}$, and $10^{-9}$ M, compared to control, in both the absence and presence of 2.8 mM glucose. Results are means of triplicates & SEM; *$P<0.05$, $P<0.01$, *$P<0.001$, from relative basal control.
Figure 2D:
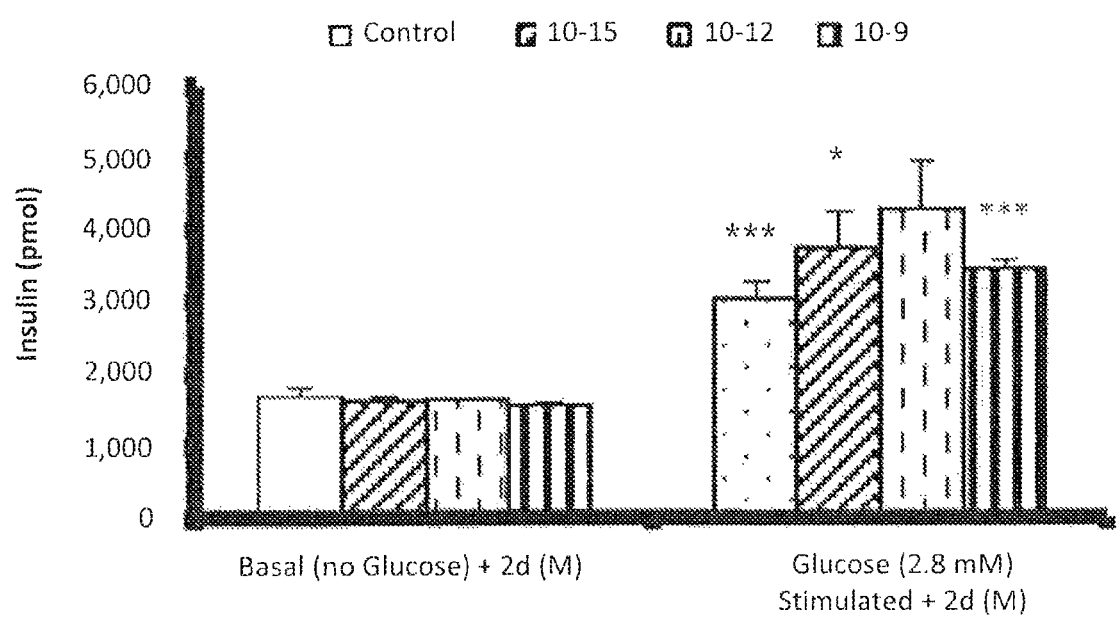
FIG. 2D is a bar graph showing the in vitro effects on insulin secretion of compound 2d at concentrations of $10^{-15}$, $10^{-12}$, and $10^{-9}$ M, compared to control, in both the absence and presence of 2.8 mM glucose. Results are means of triplicates±SEM; *$P<0.05$, $P<0.01$, *$P<0.001$, from relative basal control.

FIGS. 2B to 2D show the in-vitro effects of compounds 2b-d, respectively, at $10^{-15}$, $10^{-12}$, and $10^{-9}$ M concentrations on insulin secretion in the absence and presence of 2.8 mM glucose.

In the absence of glucose, compounds 2b-d did not significantly stimulate insulin secretions compared to the basal control. In presence of 2.8 mM glucose, compounds 2b-d stimulated insulin secretions significantly compared to basal insulin secretion. Compound 2c at $10^{-9}$ M also significantly potentiated the glucose-stimulated insulin secretion.

Example 3

Evaluation of Cycloheptylamine Derivatives 6, 9c, 9d, 9f, 10, and 11 on Fasting, Blood Glucose The same testing procedure was used as in Example 2 above, to evaluate the effect of cycloheptylamine derivatives 6, 9c, 9d, 9f, 10, and 11, provided below:

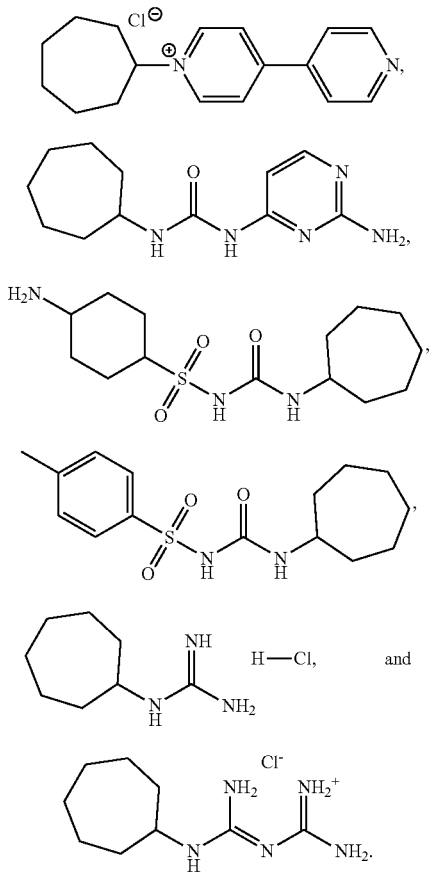

FIGS. 3A-3F show the in-vitro effects on insulin secretion demonstrated by cycloheptylamine derivatives at $10^{-15}$, $10^{-12}$, and $10^{-9}$ M concentrations, in both the absence and presence of 2.8 mM glucose.

Figure 3A:
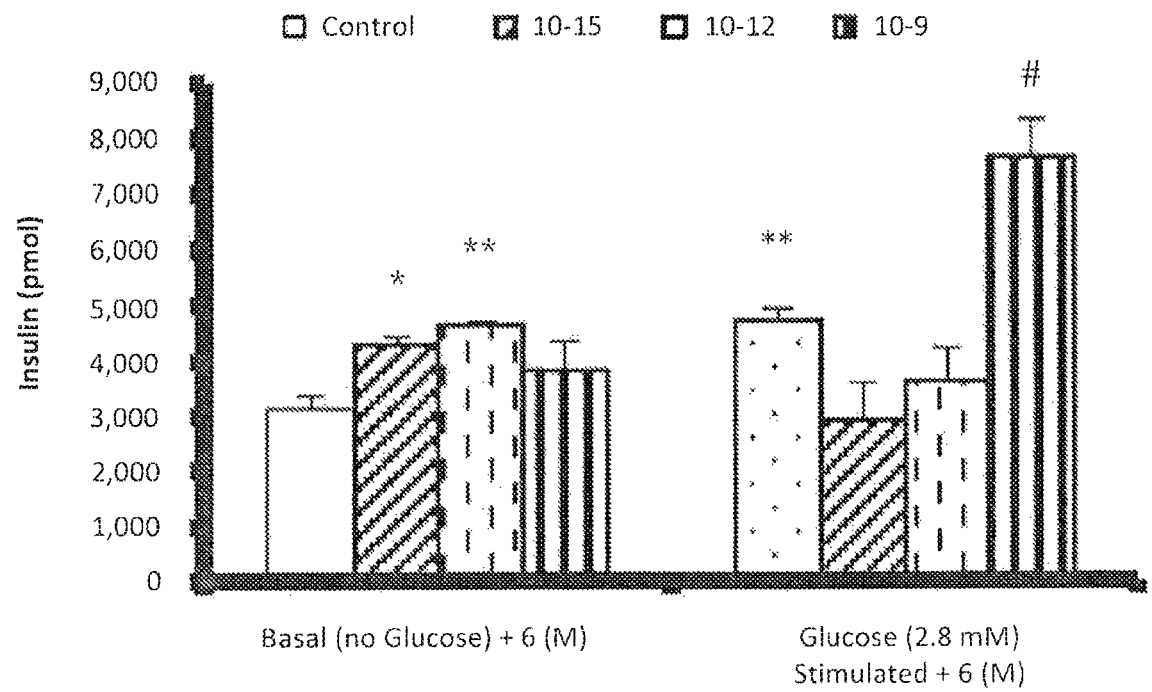
FIG. 3A is a bar graph showing the in vitro effect on insulin secretion of compound 6 at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
Figure 3B:
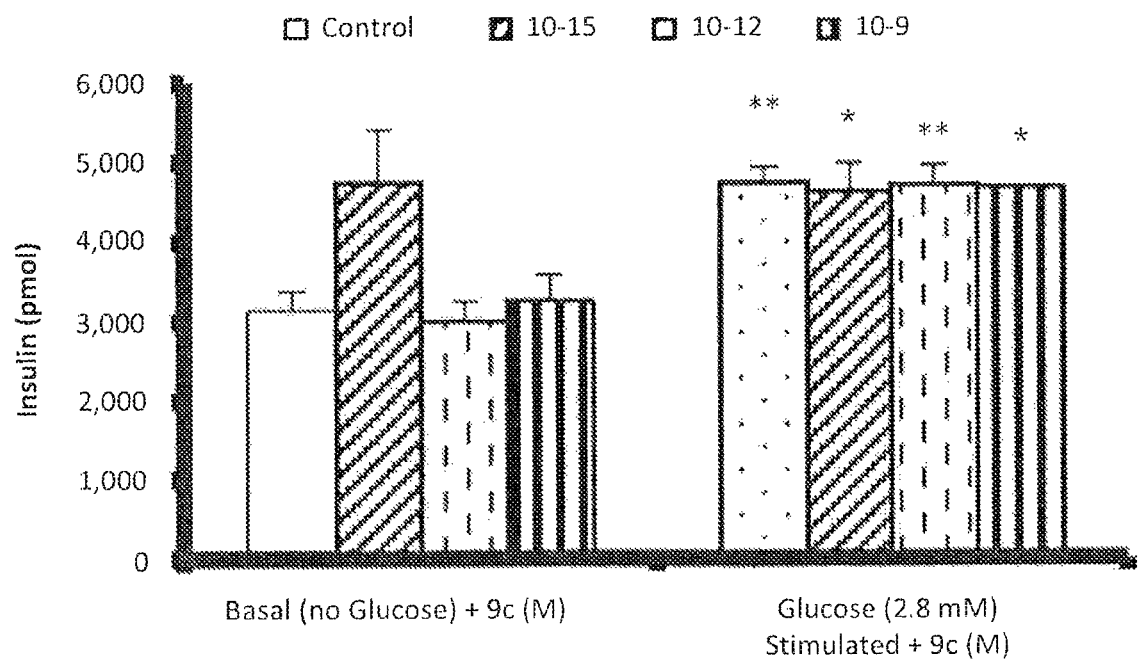
FIG. 3H is a bar graph showing the in vitro effect on insulin secretion of compound 9c at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
FIG. 3C is a bar graph showing the in vitro effect on insulin secretion of compound 9d at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
FIG. 3D is a bar graph showing the in vitro effect on insulin secretion of compound 9f at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
FIG. 3E is a bar graph showing the in vitro effect on insulin secretion of compound 10 at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
FIG. 3F is a bar graph showing the in vitro effect on insulin secretion of compound 11 at concentrations of $10^{-15}$, $10^{-12}$, and $10^{-9}$ M, compared to control, in both the absence and presence of 2.8 mM glucose. Results are means of triplicates±SEM; *P<0.05, **P<0.01, from relative basal control, and #P<0.05, ##P<0.01 from glucose 2.8 mM.
Figure 3C:
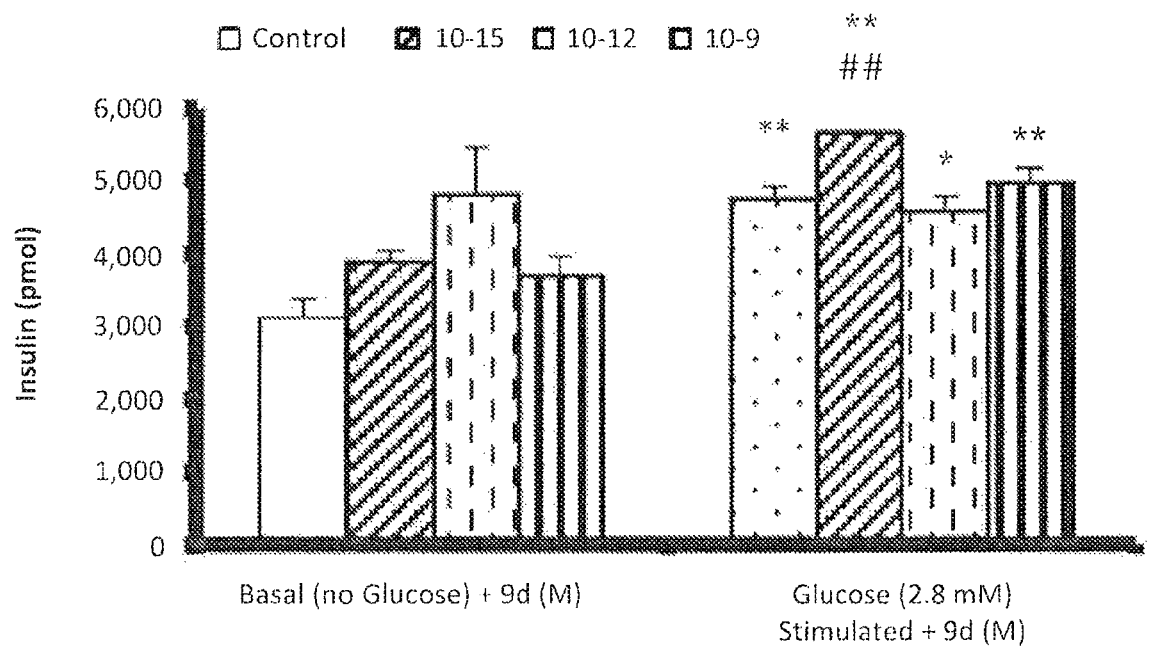
Figure 3D:
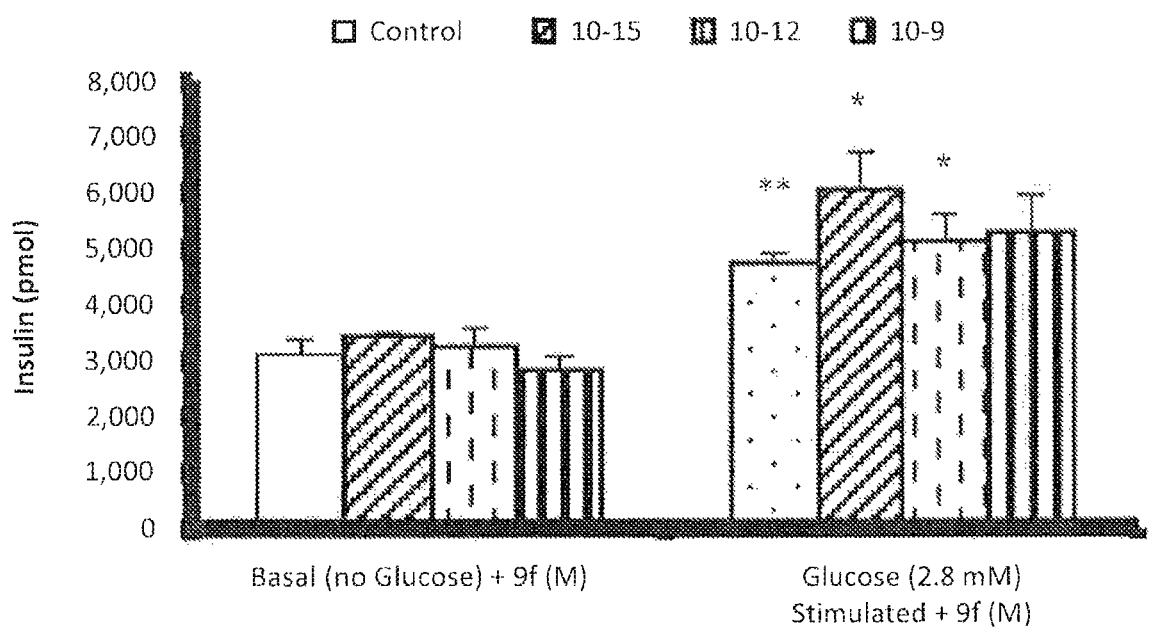
Figure 3E:
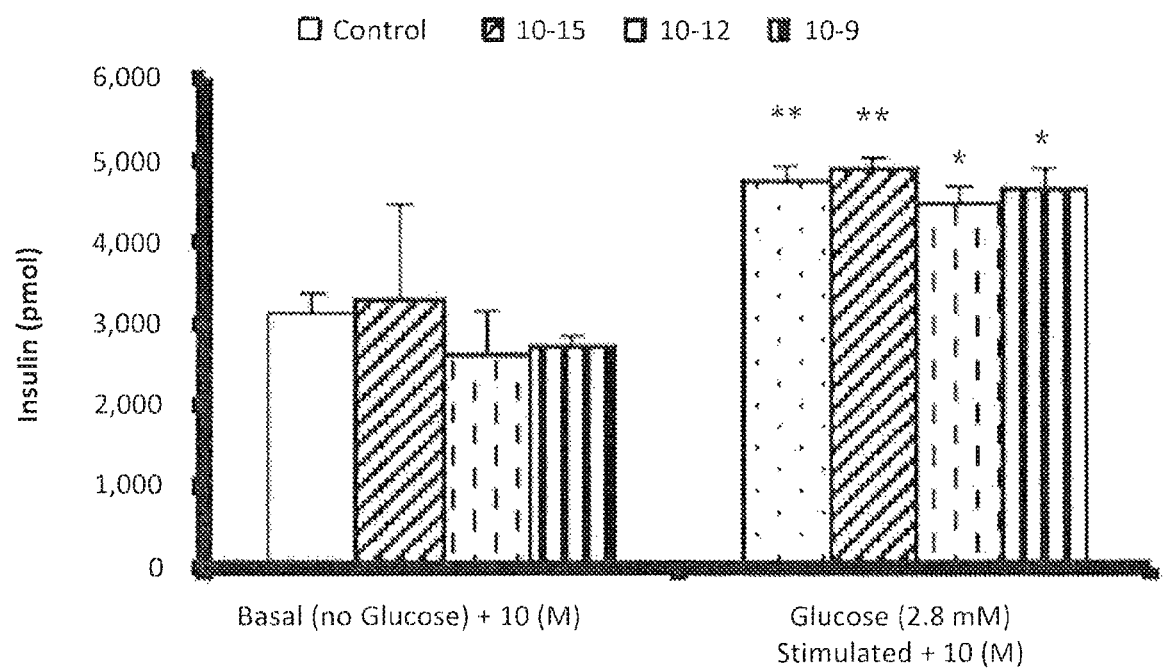
Figure 3F:
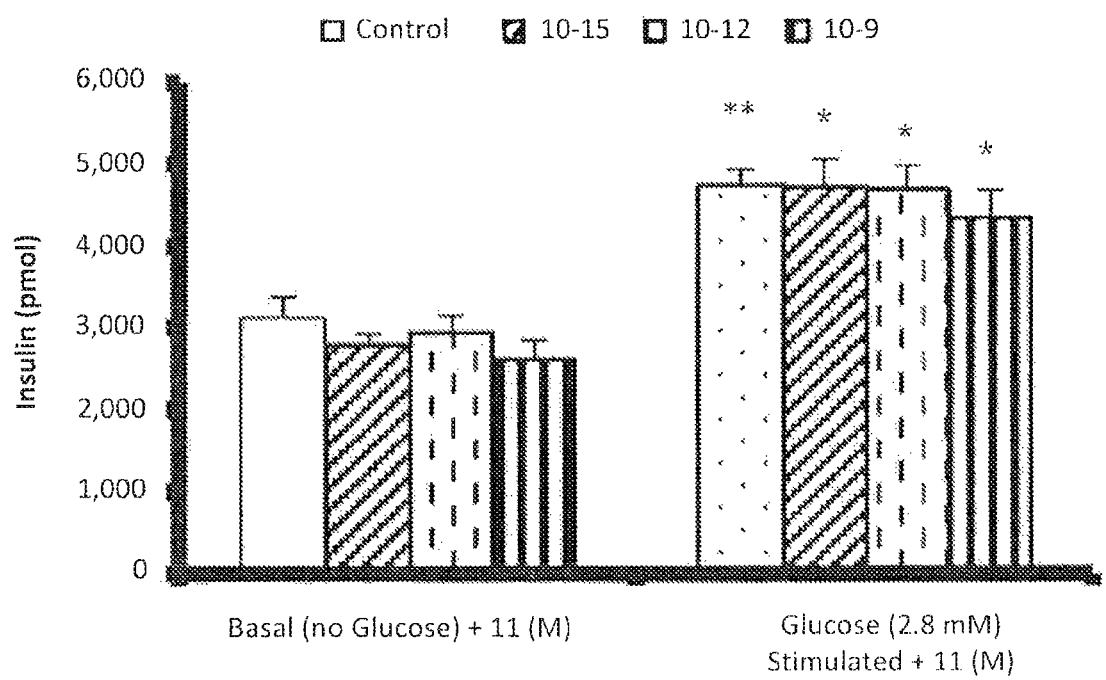

Compound 6 significantly stimulated insulin secretions compared to the basal control. In the presence of 2.8 mM glucose, compound 6 significantly stimulated insulin secretions compared to basal insulin secretion as well as insulin secretion in the presence of glucose (FIG. 3A). Compounds 9c, 9d, 9f, 10, and 11 each demonstrated significant stimulation of insulin secretion in the presence of 2.8 mM glucose, though not to a statistically significant degree in the absence of glucose (FIGS. 3B to 3F).

Example 4

Synthesis of Cycloalkylamine Hydrochloride Salts

Figure 4:
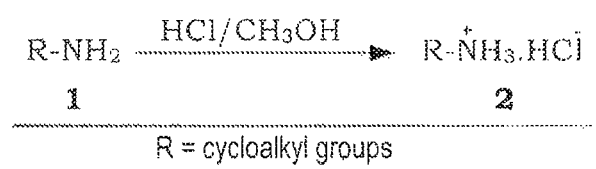
FIG. 4 depicts the synthesis scheme for cycloalkylamine derivatives 2a-d.
Figure 4:
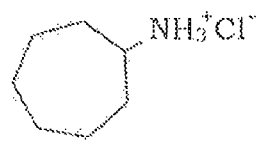
Figure 4:
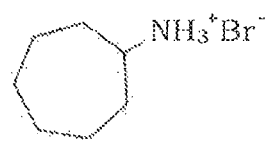
Figure 4:
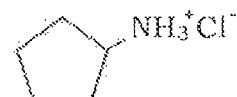
Figure 4:
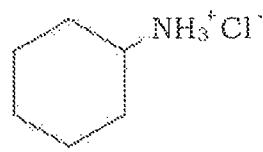

The following method was used to synthesize the desired derivatives, provide better yields, in shorter time, yielding high purities. An exemplary reaction scheme for synthesizing cycloalkylamine salts (compounds 2a-2d) is provided in FIG. 4, where R represents cycloalkyl groups.

General Procedure for the Synthesis of Cycloalkylamine Hydrochloride Salts

Cycloalkyl amine derivative was dissolved in a minimal amount of methanol and treated with excess hydrochloric acid or hydrobromic acid to form chloride or bromide salt. The salt was collected from diethyl ether using vacuum filtration to provide compounds 2a-d.

Production of compounds 2a and 2b involved use of cycloalkylamine derivatives in excess of HCl or HBr, respectively. Compound 2c was prepared using cyclopentylamine and excess HCl where, compound 2d was prepared using cyclohexylamine and excess HCl.

Analysing Result

Cycloheptanamine Hydrochloride (2a)

Off white solid, yield: 94%, mp 217-218° C.; $^1$H-NMR (DMSO-$d_6$) (δ, ppm): 1.36-1.60 (m, 10H, cycloheptyl ring), 1.82 (m, 2H, cycloheptyl ring), 3.98 (m, 1H, cycloheptyl ring), 8.24 (brs, 3H, NH$_3$, cycloheptylamine, D$_2$O-exchange); $^{13}$C-NMR (DMSO-$d_6$) (δ, ppm): 23.2, 27.2, 32.3, 52.7; Anal. Calcd for $C_7H_{16}ClN$: C, 56.18; H, 10.78; N, 9.36. Found: C, 56.63; H, 10.85; N, 9.64.

Cycloheptanamine Hydrobromide (2b)

Off white solid, yield: 93%, mp 213-214° C.; $^1$H-NMR (DMSO-$d_6$) (δ, ppm): 1.36-1.61 (m, 10H, cycloheptyl ring), 1.86-1.88 (m, 2H, cycloheptyl ring), 3.90 (m, 1H, cycloheptyl ring), 6.60 (brs, 3H, NH$_3$ (cycloheptylamine, D$_2$O-exchange); $^{13}$C-NMR (DMSO-$d_6$) (δ, ppm): 22.8, 26.8, 31.9, 52.3; Anal. Calcd for $C_7H_6BrN$: C, 43.31; H, 8.31; N, 7.22; Found: C, 43.76; H, 8.38; N, 7.50.

Cycloheptanamine hydrochloride (2c)

Off white solid, yield: 91%, nip 209-211° C.; $^1$H-NMR (CDCl$_3$, 400 MHz) (δ, ppm): 1.64-1.65 (m, 2H, cyclopentyl ring), 1.85-2.05 (m, 5H, cyclopentyl ring), 2.31 (m, 1H, cyclopentyl ring), 3.65 (m, 1H, cyclopentyl ring), 8.27 (brs, 3H, NH$_3$, cyclopentylamine, D$_2$O-exchange); $^{13}$C-NMR (CDCl$_3$, 100 MHz) (δ, ppm): 23.5, 30.5, 52.1 (cyclopentyl ring); Anal. Calcd for $C_5H_{12}ClN$: C, 49.38; H, 9.95; N, 11.52. Found: C, 49.83; H, 10.02; N, 11.80.

Cycloheptanamine hydrochloride (2d)

Light brown solid, yield: 92%, nip 215° C.; $^1$H-NMR (DMSO-$d_6$) (δ, ppm): 1.33 (m, 4H, cyclohexyl ring), 1.59 (m, 4H, cyclohexyl ring), 2.90 (m, 2H, cyclohexyl ring), 3.58 (m, 1H, cyclohexyl ring), 7.38 (s, 3H, NH$_3$ (cyclohexylamine, D$_2$O-exchange); $^{13}$C-NMR (DMSO-$d_6$) (δ, ppm): 24.8, 25.6, 33.1, 48.5 (cyclohexyl ring); Anal. Calcd for $C_6H_{14}ClN$: C, 53.13; 1, 10.40; N, 10.33. Found: C, 53.58; H, 10.47; N, 10.61.

Synthesis of Cycloheptanamine Derivatives

Example 5

Cycloheptylamine derivatives were prepared according to the reaction scheme depicted in FIG. 5.

Synthesis of Compound 6

4,4'-bipyridine (10 mmol, 1.56 g) and 1-chloro-2,4-dinitrobenzene (10 mmol, 2.02 g) were dissolved in 5 ml acetone and the vessel was closed immediately and subjected to microwave irradiation at 58° C. for about 20 min. The precipitate was collected by filtration, washed with diethyl ether, and dried under vacuum to afford the final product, 1-(2,4-dinitrophenyl)-[4,4'-bipyridin]-1-ium (5), as a light green powders (3.26 g, yield: 91%); $^1$H-NMR [CDCl$_3$, 400 MHz]: (δ, ppm) 7.87 (d, 2H, aromatic, J=4.0 Hz), 8.13 (d, 1H, aromatic, J=8.0 Hz), 8.53 (d, 2H, aromatic, J=4.0 Hz), 8.67 (d, 2H, J=8.0 Hz), 8.79 (d, 1H, aromatic, J=8.0 Hz), 9.10 (d, 2H, aromatic, J=8.0 Hz), 9.23 (s, H, aromatic); $^{13}$C-NMR [CDCl$_3$, 100 MHz]: (δ, ppm) 156.89, 150.00, 149.54, 145.69, 142.84, 141.97, 138.32, 131.07, 130.51, 126.03, 122.63, 122.60.

Compound 5 (2 mmol, 0.65 g) from (Example 5) was dissolved in 3 mL ethanol/water (1:1 by volume ratio), and corresponding cycloheptylamine (2.4 mmol, 0.31 ml) was added. The mixture was subjected to microwave irradiation at 130° C. for 30 min. The precipitate formed and after filtering, compound 6 (1-cycloheptyl-[4,4'-bipyridin]-1-ium chloride (6)) was isolated as dark-gray in yield 89%, mp 102° C., IR (KBr, cm$^{-1}$): 3023 (C—H aromatic), 2927 (C—H aliphatic), 1638 (C=N); $^1$H-NMR (D$_2$O, 400 MHz]: (δ, ppm) 1.44-2.08 (m, 12H, cycloheptyl ring), 4.69 (m, 1H, cycloheptyl ring), 7.66 (d, 2H, J=6.3 Hz), 8.14 (d, 2H, J=6.7 Hz), 8.52 (d, 2H, J=6.3 Hz), 8.78 (d, 2H, J=6.7 Hz); $^{13}$C-NMR (D$_2$O, 400 MHz]: (δ, ppm) 23.9, 26.4, 35.4, 73.8 (cycloheptyl ring), 122.3, 125.8, 142.5, 143.0, 149.8, 153.3 (bipyridine ring); Anal. Calcd for C$_{17}$H$_{21}$ClN$_2$: C, 70.70; H, 7.33; N, 9.70; Found: C, 71.15; H, 7.40; N, 9.46.

Example 7

Synthesis of Compound 8

Compound 8 was prepared according to the reaction scheme depicted in FIG. 6. N1,N2-dicycloheptyloxalamide (8). Oxalyl chloride (0.46 mmol, 0.04 ml) in dry dichloromethane (5 ml) was added dropwise to a solution of cycloheptylamine (0.61 mmol, 0.08 ml) in dry dichloromethane (10 ml) containing triethylamine (0.61 mmol, 0.62 ml) (See FIG. 6). The reaction mixture was stirred at room temperature for 1.5 h. The solvent was then evaporated and the residue was quenched with water. The resulting precipitate was filtered, dried and recrystallized from methanol to yield compound 8 (92%) as a pale yellow solid, mp 232° C., IR (KBr, cm$^{-1}$): 3299 (NH), 3042 (C—H aromatic), 2930 (C—H aliphatic), 1651 (C=O); $^1$H-NMR [CDCl$_3$, 400 MHz]: (δ, ppm) 1.47-1.93 (m, 24H, cycloheptyl ring), 3.88-3.90 (m, 2H, cycloheptyl ring), 7.44 (br, 2H, —NH, D$_2$O-exchangeable); $^{13}$C NMR[CDCl$_3$, 100 MHz]: (δ, ppm) 23.9, 27.9, 34.6, 50.9 (cycloheptyl ring), 158.7 (C=O); Anal. Calcd for C$_{16}$H$_{28}$N$_2$O$_2$: C, 68.53; H, 10.06; N, 9.99. Found: C, 68.98; H, 10.13; N, 10.27.

Example 8

Synthesis of Cycloheptyl-Urea Derivatives

Compounds 9a-f were prepared according to the reaction scheme depicted in FIG. 6 (with R and R$_1$ defined in the table depicted in FIG. 7). To a solution of the respective amine (10 mmol, 2.31 g) in acetonitrile (15 ml), the respective isocyanate derivative was added (FIGS. 7 and 8). The reaction mixture was stirred at room temperature for 2-3 hrs. The progress of the reaction was monitored by TLC and after completion; the precipitate formed was filtered, washed with ethanol, and dried to give the product, compounds 9a-f, shown below:

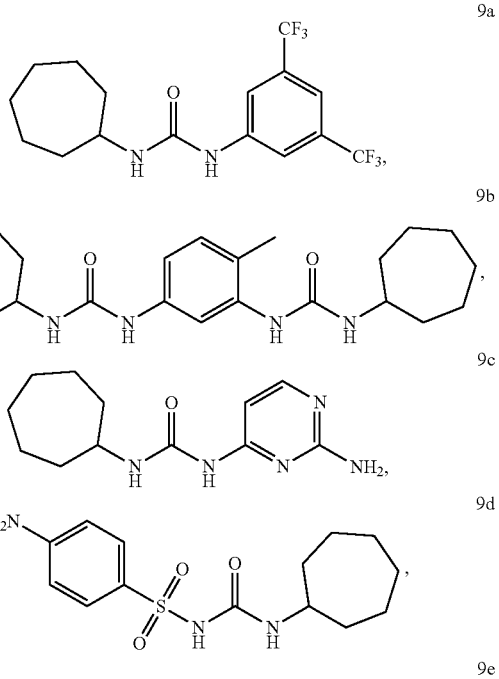

1-[3'5-Bis(trifluoromethyl)phenyl]-3-cycloheptylurea (9a). White solid, yield: 91%, mp 169-170° C.; IR (KBr, cm$^{-1}$): 3340 (N—H urea), 3122 (C—H aromatic), 2930 (C—H aliphatic), 1659 (C=O, urea); $^1$H-NMR [DMSO-d$_6$, 400 MHz]: (δ, ppm) 1.41-1.54 (m, 10H, cycloheptyl ring), 1.78-1.79 (m, 2H, cycloheptyl ring), 3.80-3.82 (m, 1H, cycloheptyl ring), 6.41 (d, 1H, —NH, D$_2$O-exchangeable, J=8.0 Hz), 7.50 (s, 1H, aromatic), 8.03 (s, 2H, aromatic), 9.01 (s, 1H, —NH, D$_2$O-exchangeable); $^{13}$C-NMR [DMSO-d$_6$, 100 MHz]: (δ, ppm) 23.9, 28.1, 35.1, 50.7 (cycloheptyl ring), 113.7, 117.5 (aromatic), 119.7-127.9 (CF$_3$), 130.5-131.5 (aromatic), 143.0 (aromatic), 154.8 (C=O, urea); Anal. Calcd for C$_{16}$H$_{18}$F$_6$N$_2$O: C, 52.18; H, 4.93; N, 7.61. Found: C, 52.63; H, 5.00; N, 7.89.

1,1'-(4"-Methyl-1",3"-phenylene) bis(3-cycloheptylurea) (9b). White solid, yield: 78%, mp 281-282° C.; IR (KBr, cm$^{-1}$): 3319 (N—H urea), 2927 (C—H aliphatic), 1638 (C=O, urea); $^1$H-NMR [DMSO-d$_6$, 400 MHz]: (δ, ppm) 1.56-1.73 (n, 20H, cycloheptyl ring), 2.06 (m, 4H, cycloheptyl ring), 2.16 (s, 3H, CH$_3$), 4.17 (m, 2H, cycloheptyl ring), 5.42 (d, 2H, —NH, D$_2$O-exchange, J=8.0 Hz), 7.21 (s, 1H, aromatic), 7.48-7.50 (m, 2H, aromatic), 8.05 (brs, 2H, —NH, D$_2$O-exchange); $^{13}$C-NMR [DMSO-d$_6$, 100 MHz]: (δ, ppm) 11.8 (CH$_3$), 23.9, 28.1, 35.3, 50.2 (cycloheptyl ring), 114.7, 117.8, 127.1, 129.1, 131.2, 136.2 (aromatic), 154.7 ((0, urea); Anal. Calcd for C$_{23}$H$_{36}$N$_4$O$_2$: C, 68.97; H, 9.06; N, 13.99. Found: C, 69.42; H, 9.13; N, 14.27.

1-(2'-Aminopyrimidin-4'-yl)-3-cycloheptylurea (9c). White solid, yield: 80%, mp 139-141° C.; IR (KBr, cm$^{-1}$): 3477, 3405 (NH$_2$), 3307 (N—H urea), 2927 (C—H aliphatic), 1699 (C=O, urea), 1535 (C=C aromatic); $^1$H-NMR [DMSO-d$_6$, 400 MHz]: (δ, ppm) 1.25-1.55 (m, 10H, cycloheptyl ring), 1.70-1.75 (m, 2H, cycloheptyl ring), 3.89-3.94 (m, 1H, cycloheptyl ring), 5.56 (d, 1H, NH, cycloheptylamine, D$_2$O-exchange, J=8.0 Hz), 5.63 (d, 1H, H$_5$-pyrimidine ring, J=6.0 Hz), 6.19 (brs, 2H, NH$_2$, D$_2$O-exchange), 7.01 (brs, 1H, NH, D$_2$O-exchange), 7.58 (d, 1H, H$_6$-pyrimidine ring, J=6.0 Hz); $^{13}$C-NMR [DMSO-d$_6$, 100 MHz]: (δ, ppm) 23.9, 28.2, 35.5, 50.1 (cycloheptyl ring), 95.4 (C5-pyrimidine), 154.7 (C6-pyrimidine), 156.3 (C4-pyrimidine), 163.8 (C=O, urea), 164.5 (C2-pyrimidine); Anal. Calcd for C$_{12}$H$_{19}$N$_5$O: C, 57.81; H, 7.68; N, 28.09. Found: C, 58.25; H, 7.75; N, 28.37.

4-Amino-N-(cycloheptylcarbamoyl)benzenesulfonamide (9d). White solid, yield: 91%, mp 235-236° C.; IR (KBr, cm$^{-1}$): 3384,3349 (NH$_2$), 3190 (N—H urea), 2924 (C—H aliphatic), 1683 (C=O, urea), 1597 (C=C aromatic), 1310, 1150 (—SO$_2$NH$_2$); $^1$H-NMR [DMSO-d$_6$, 400 MHz]: (δ, ppm) 1.34-1.61 (m, 10H, cycloheptyl ring), 1.88 (m, 2H, cycloheptyl ring), 3.63-3.68 (m, 1H, cycloheptyl ring), 5.79 (s, 2H, NH$_2$, D$_2$O-exchangeable, J=8.0 Hz), 6.54 (d, 2H, aromatic, J=6.0 Hz), 7.27 (brs, 1H, —NH, D$_2$O-exchangeable), 8.22 (d, 2H, aromatic, J=8.0 Hz), 10.45 (s, 1H, —NH, D$_2$O-exchangeable); $^{13}$C-NMR [DMSO-d$_6$, 100 MHz]: (δ, ppm) 23.5, 27.7, 32.8, 51.9 (cycloheptyl ring), 112.8, 127.2, 133.1, 152.4 (aromatic), 161.6 (C=O, urea); Anal. Calcd for C$_{14}$H$_{21}$N$_3$O$_3$S: C, 54.00; H, 6.80; N, 13.49; S, 10.30. Found: C, 54.45; H, 6.87; N, 13.77; S, 10.57.

4-(3'-Cycloheptylureido)-N-(5"-methylisoxazol-3"-yl)benzenesulfonamide (9e). White solid, yield 82%, mp 245° C.; IR (KBr, cm$^{-1}$): 3360 (NH), 3108 (C—H aromatic), 2932 (C—H aliphatic), 1688 (C=O), 1590 (C=C aromatic); $^1$H-NMR [DMSO-d$_6$, 400 MHz]: (δ, ppm) 1.40-1.53 (m, 10H, cycloheptyl ring), 1.77 (m, 2H, cycloheptyl ring), 2.26 (s, 3H, CH$_3$), 3.64 (m, 1H, cycloheptyl ring), 6.09 (s, 1H, aromatic), 6.27 (d, 1H, —NH, D$_2$O-exchange, J=8.0 Hz), 7.50 (d, 2H, aromatic. J=8.0 Hz), 7.65 (d, 2H, aromatic, J=8.0 Hz), 8.77 (s, 1H, —NH, D$_2$O-exchange), 11.19 (s, 1H, —NH, D$_2$O-exchange); $^{13}$C-NMR [DMSO-d$_6$, 100 MHz]: (δ, ppm) 12.5 (CH$_3$), 21.4, 25.4, 30.5, 56.5 (cycloheptyl ring), 95.7 (methylisoxazole C), 112.9, 129.3, 135.2, 142.9 (aromatic), 153.7 (methylisoxazole C), 158.4 (C=O), 170.3 (methylisoxazole C); Anal. Calcd for C$_{18}$H$_{24}$N$_4$O$_4$S: C, 55.08; H, 6.16; N, 14.28; S, 8.17; Found: C, 55.51; H, 6.22; N, 14.55; S, 8.15.

N-(Cycloheptylcarbamoyl)-4-methylbenzenesulfonamide (9f). White solid, yield: 94%, mp 241° C.; IR (KBr, cm$^1$): 3142 (N—H urea), 2932 (C—H aliphatic), 1655 (C=O, urea); $^1$H-NMR [DMSO-d$_6$, 400 MHz]: (δ, ppm) 1.34-1.61 (m, 10H, cycloheptyl ring), 1.86-1.88 (m, 2H, cycloheptyl ring), 2.28 (s, 3H, CH$_3$), 3.63-3.68 (m, 1H, cycloheptyl ring), 7.12 (d, 2H, phenyl ring, J=8.0 Hz), 7.55 (d, 2H, phenyl ring, J=8.0 Hz) 7.65 (brs, 2H, NH, D$_2$O-exchange); $^{13}$C-NMR [DMSO-d$_6$, 100 MHz]: (δ, ppm) 23.5 (CH$_3$), 27.5, 32.8, 52.1, 58.9 (cycloheptyl ring), 127.2, 128.4, 136.2, 137.7 (phenyl ring), 163.3 (C=O, urea); Anal. Calcd for C$_{15}$H$_{22}$N$_2$O$_3$S: C, 58.04; H, 7.14; N, 9.02; S, 10.33. Found: C, 58.49; H, 7.21; N, 9.30; S, 10.61.

Example 9

Synthesis of Cycloheptyl Guanidine Derivatives

Figure 9:
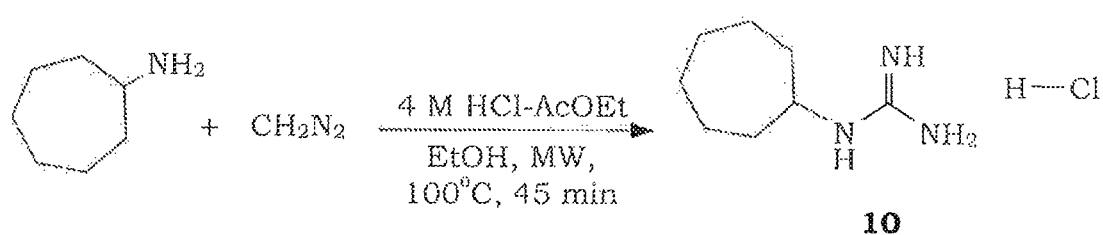
FIG. 9 depicts the synthesis scheme for compound 10.
Figure 10:
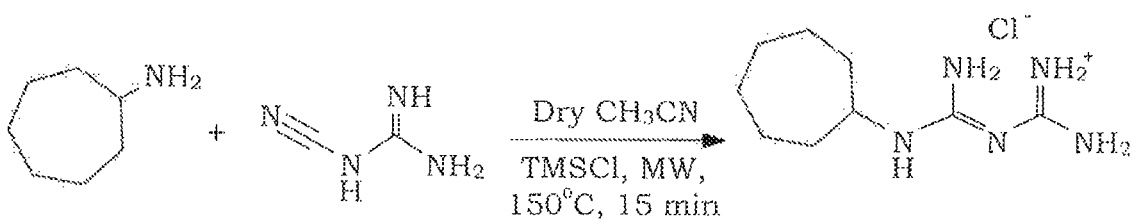
FIG. 10 depicts the synthesis scheme for compound 11.

Referring to FIGS. 9 and 10, a mixture of cycloheptylamine (1 mmol, 0.11 g), cyanamide (1 mmol, 0.04 g), 4 M HCl—AcOEt (0.1 ml) and EtOH (2 ml) was subjected to microwave irradiation at 100° C. for 45 min. The precipitated solid was filtered and washed with AcOEt and H$_2$O to give compound 10, having the following structural formula:

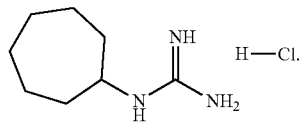

1-Cycloheptylguanidine hydrochloride (10): Off-white solid, yield 64%, mp 106° C.; IR (KBr, cm$^{-1}$): 3429, 3388 (NH$_2$), 3147 (N—H), 2930 (C—H aliphatic), 1560 (C=C aromatic); $^1$H-NMR [DMSO-d$_6$, 400 MHz]: (δ, ppm) 1.38-1.68 (m, 10H, cycloheptyl ring), 1.80-1.81 (m, 21, cycloheptyl ring), 3.93-3.95 (m, 1H, cycloheptyl ring), 4.13-4.15 (brs, 1H. —NH, D$_2$O-exchange), 6.68 (brs, 2H, —NH.HCl, D)$_2$O-exchange), 8.03 (brs, 2H, NH$_2$, D$_2$O-exchange); $^{13}$C-NMR [DMSO-d$_6$, 100 MHz]: (δ, ppm) 21.4, 25.4, 30.5, 50.2 (cycloheptyl ring), 160.2 (C=NH); Anal. Calcd for C$_8$H$_{18}$ClN$_3$: C, 50.12; H, 9.46; N, 21.92. Found: C, 50.52; H, 9.53; N, 22.20.

Cycloheptylamine (2.1 mmol, 254.5 mg) was added to a solution of dicyandiamide (2.1 mmol, 176.6 mg) in 3.7 ml of dry CH$_3$CN, and TMSCl (trimethylsilyl chloride) (2.3 mmol, 228.1 mg) was slowly added dropwise to the mixture. The mixture was stirred and irradiated for 15 minutes at 150° C., using microwave reactor. After the mixture was cooled down to approximately 50° C., isopropyl alcohol (6.3 mmol, 0.49 ml) was added slowly, and the mixture was further stirred and irradiated at 125° C. for 1 minute. The precipitation of the biguanide hydrochloride salt was washed with CH$_3$CN twice to afford compound 11, having the structural formula shown below:

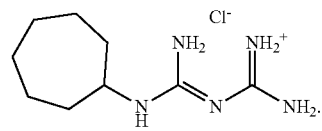 [SMILES: NC(=[NH2+])/N=C(\N)NC1CCCCCC1 ; [Cl-]]

(E)-Amino[(amino(cycloheptylamino)methylene)amino]methaniminium chloride (11). The analytical sample of compound 11 was obtained by recrystallization from iPrOH as a white powder; yield 61%, mp 283° C.; IR (KBr, cm$^{-1}$): 3439, 3335 (NH$_2$), 3192 (N—H), 2925 (C—H aliphatic), 1560 (C=C aromatic); $^1$H-NMR [DMSO-d$_6$, 400 MHz]: (δ, ppm) δ 1.40-1.59 (m, 10H, cycloheptyl ring), 1.78 (m, 2H, cycloheptyl ring), 3.64 (m, 1H, cycloheptyl ring), 5.19 (brs, 1H, —NH, D$_2$O-exchange), 6.84 (brs, 2H, —NH.HCl, D$_2$O-exchange), 8.23 (brs, 4H, NH$_2$, D$_2$O-exchange); $^{13}$C-NMR [DMSO-d$_6$, 100 MHz]: (δ, ppm) 23.5, 27.7, 32.5, 52.0 (cycloheptyl ring), 160.8 (C=N), 163.3 (C=N); Anal. Calcd for C$_9$H$_{20}$ClN$_5$: C, 46.25; H, 8.62; N, 29.96. Found: C, 46.70; H, 8.69; N, 30.24.

It is to be understood that the cycloalkylamine derivatives and methods disclosed here are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating diabetes comprising administering a therapeutically effective amount of Cycloalkylamine derivatives, comprising compounds selected from the group consisting of cycloheptylamine hydrochloride, cycloheptylamine hydrobromide, cyclopentylamine hydrochloride, cyclohexylamine hydrochloride, or a pharmaceutically acceptable salt thereof to a patient in need thereof.

2. The method of claim 1, wherein the diabetes is type-2 diabetes.

3. The method of claim 1, wherein the therapeutically effective amount produces a decrease in plasma glucose levels in the patient.

4. The method of claim 1, wherein the therapeutically effective amount produces an increase in the insulin secretion in the patient.

* * * * *